(12) United States Patent
Takahashi et al.

(10) Patent No.: US 9,001,972 B2
(45) Date of Patent: Apr. 7, 2015

(54) RADIATION IMAGE DETECTION APPARATUS AND RADIATION IMAGE PHOTOGRAPHING SYSTEM

(71) Applicant: FUJIFILM Corporation, Tokyo (JP)

(72) Inventors: Yasufumi Takahashi, Kanagawa (JP); Makoto Sugizaki, Kanagawa (JP); Naoto Iwakiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 321 days.

(21) Appl. No.: 13/676,654

(22) Filed: Nov. 14, 2012

(65) Prior Publication Data

US 2013/0121471 A1 May 16, 2013

(30) Foreign Application Priority Data

Nov. 15, 2011 (JP) .................. 2011-250088

(51) Int. Cl.
| | | |
|---|---|---|
| A61B 6/00 | (2006.01) | |
| H05G 1/30 | (2006.01) | |
| H05G 1/46 | (2006.01) | |
| H04N 5/32 | (2006.01) | |
| H04N 5/357 | (2011.01) | |

(52) U.S. Cl.
CPC . *H05G 1/30* (2013.01); *H04N 5/32* (2013.01); *H04N 5/357* (2013.01); *A61B 6/548* (2013.01)

(58) Field of Classification Search
USPC ............. 378/62, 87, 88, 91, 96–98, 108, 210; 382/132, 274, 325
See application file for complete search history.

(56) References Cited

U.S. PATENT DOCUMENTS

| 8,497,932 B2 * | 7/2013 | Morimoto ..................... 348/362 |
| 2006/0013465 A1 * | 1/2006 | Nonaka ......................... 382/132 |
| 2008/0107234 A1 * | 5/2008 | Amitani ....................... 378/98.5 |
| 2010/0104065 A1 * | 4/2010 | Eguchi ............................ 378/62 |
| 2013/0129053 A1 * | 5/2013 | Takahashi et al. .............. 378/91 |
| 2013/0223592 A1 * | 8/2013 | Sato ................................ 378/62 |
| 2014/0177798 A1 * | 6/2014 | Kitagawa et al. ............... 378/62 |

FOREIGN PATENT DOCUMENTS

| JP | 2002-330429 A | 11/2002 |
| JP | 2006-026083 A | 2/2006 |
| JP | 2006-81735 | 3/2006 |
| JP | 2006-87566 A | 4/2006 |
| JP | 2011-130880 A | 7/2011 |
| JP | 2011-133302 A | 7/2011 |

OTHER PUBLICATIONS

Japanese Office Action dated Dec. 3, 2013, with English translation.

* cited by examiner

*Primary Examiner* — Bernard E Souw
(74) *Attorney, Agent, or Firm* — McGinn IP Law Group, PLLC.

(57) ABSTRACT

A radiation image detection apparatus, includes: a control unit configured to drive an imaging unit so that a radiation image data is acquired, an image receiving unit is reset after acquiring the radiation image data, and a dark image data is acquired; in which: the control unit changes at least one of a reset time of the image receiving unit and a reduction ratio of an reduced image data on the basis of the communication speed by such that the transmission of the reduced image data is completed at least prior to reading-out an electrical charge signal from the image receiving unit when acquiring the dark image.

9 Claims, 10 Drawing Sheets

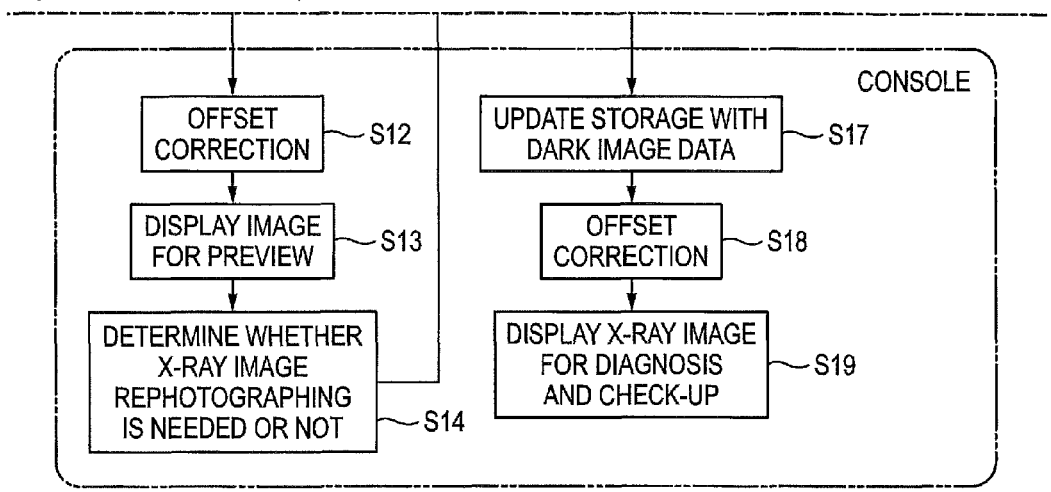

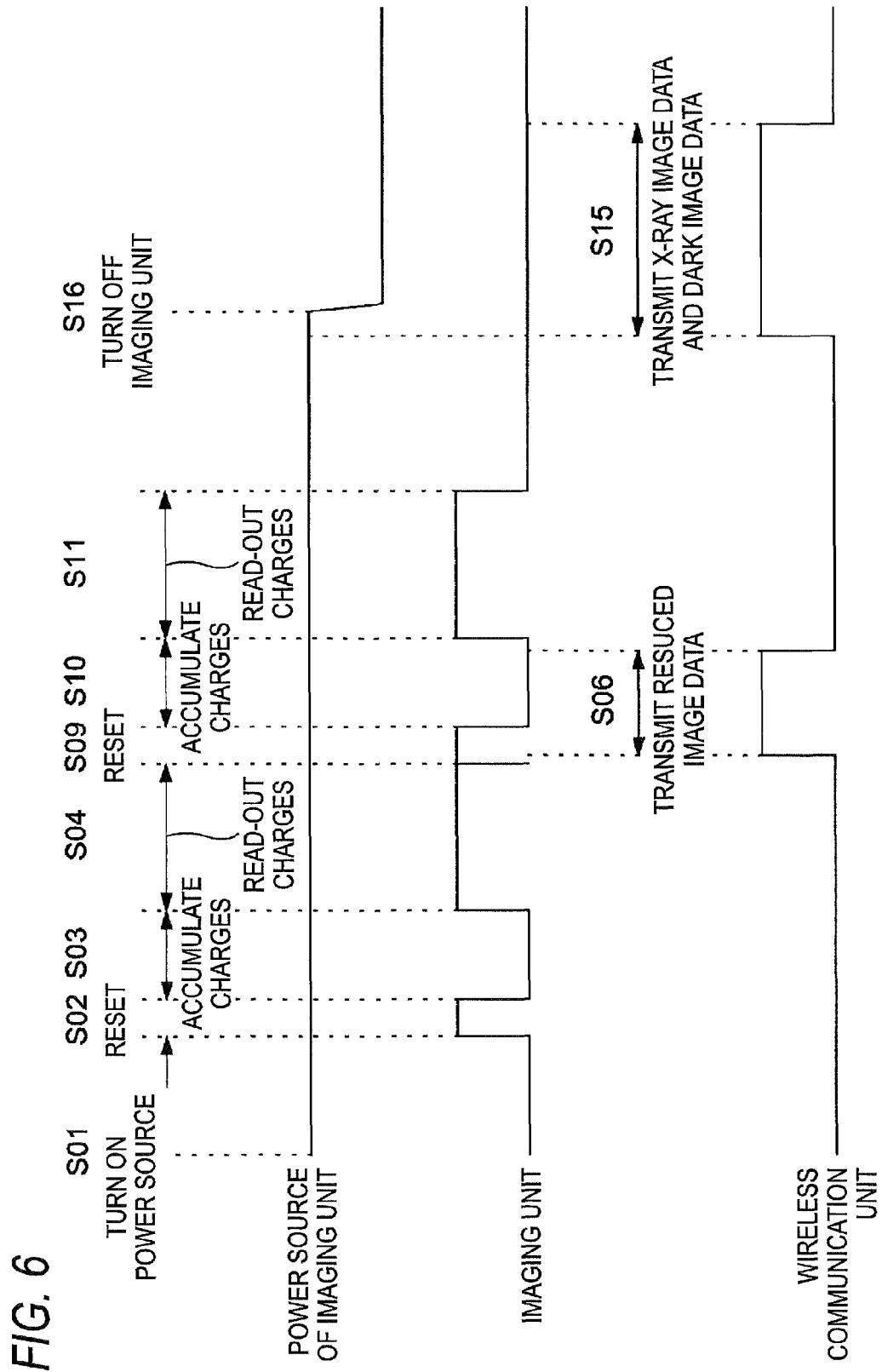

(FIG. 7 CONTINUED)
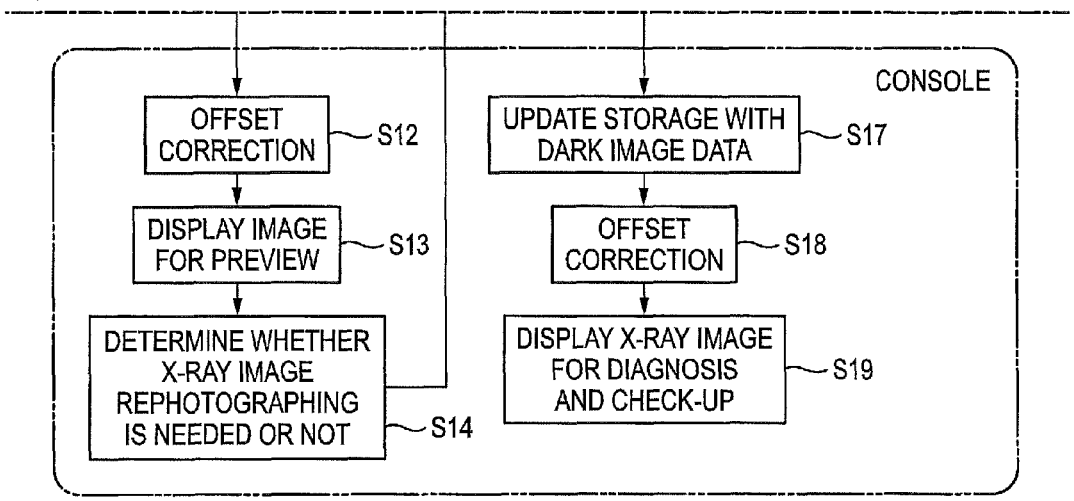

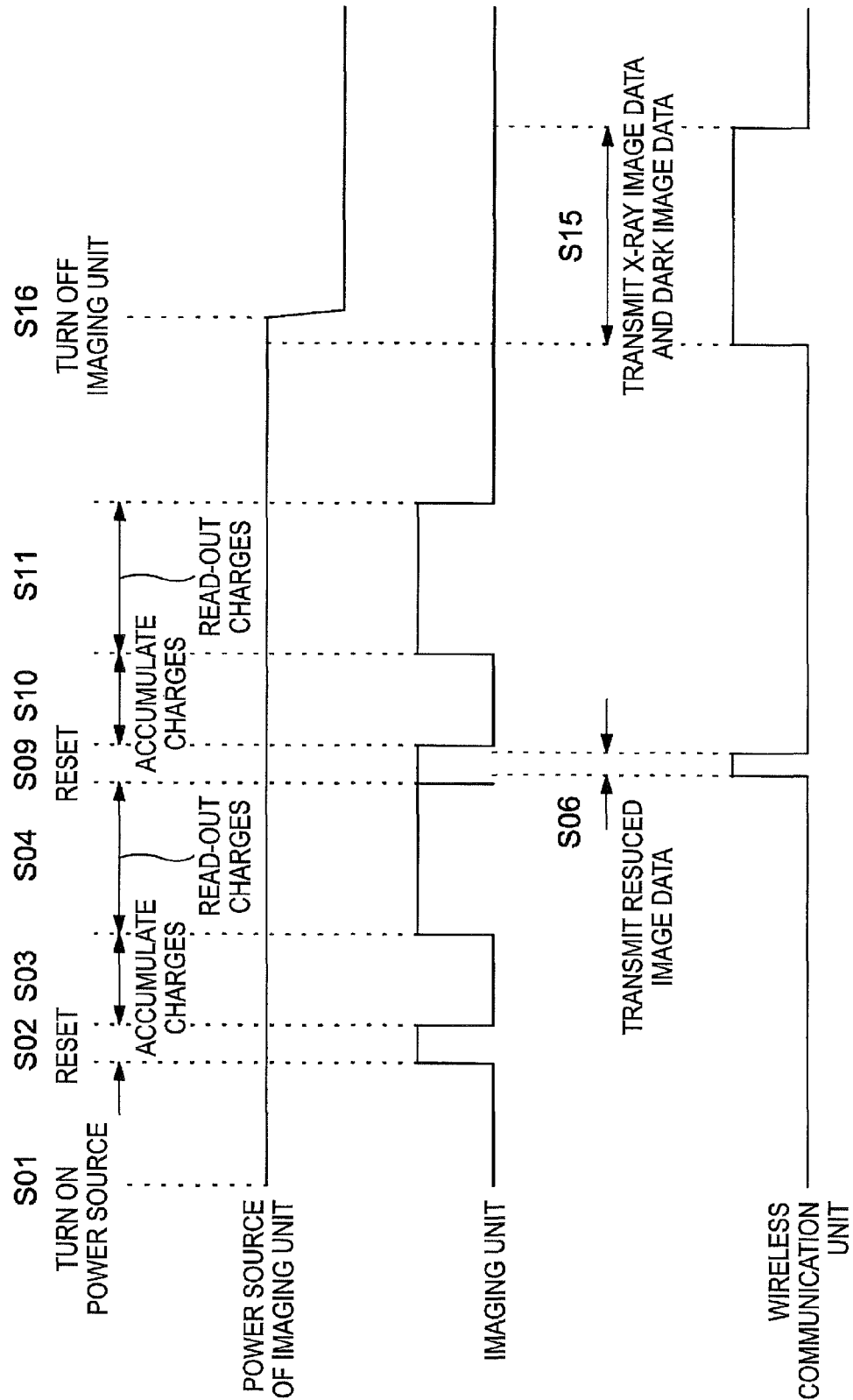

RADIATION IMAGE DETECTION APPARATUS AND RADIATION IMAGE PHOTOGRAPHING SYSTEM

CROSS-REFERENCE TO RELATED APPLICATIONS

This application is based on and claims priority under 35 USC 119 from Japanese Patent Application No. 2011-250088 filed on Nov. 15, 2011; the entire content of which is incorporated herein by reference.

BACKGROUND OF THE INVENTION

1. Technical Field

The present invention relates to a radiation image detection apparatus and a radiation image photographing system.

2. Related Art

An X-ray image photographing has been widely distributed in areas such as, for example, medical diagnoses and a non-destructive inspection. In a general X-ray image photographing, an X-ray is irradiated to a subject and attenuated while transmitting through each part of the subject. The transmitted X-ray is then detected and an X-ray image of the subject is acquired based on the intensity distribution of the transmitted X-ray.

Recently, as for a medium for detecting an X-ray, a flat panel detector (FPD) having a two-dimensional array of pixels for detecting an X-ray has been used to convert the detected X-ray into an electrical charge signal and generate a pixel data based on the charge signal output from the pixel array.

In general, various correction processes are performed on image data of a subject acquired by the FPD to present an image based on the corrected image data as the X-ray image of the subject. An example of the correction process may include an offset correction.

The offset correction removes a dark current noise of each pixel of the FPD, and the dark current is measured as an electrical signal output from each pixel while the X-ray is not irradiated to each pixel. The offset correction removes the dark current noise that is different in each pixel by subtracting the dark image data generated while the X-ray is not irradiated to the pixels from the image data generated while the X-ray is irradiated to the pixels. Dark image data is acquired in a series of photographing sequences of acquiring the X-ray image data, and for example, acquired after the X-ray image data is acquired.

In the X-ray image photographing, so called an electronic cassette configured such that the FPD is accommodated in a portable housing is widely used and the image data acquired by the electronic cassette is transmitted through a wire communication or wireless communication to a console in which the operations such as a photographing condition setting or a photographing command are conducted, and the image is displayed in the console.

Further, when the photographing result is con firmed early so that, for example, the necessity of rephotographing can be determined quickly, it is possible to smoothly perform a workflow in a diagnosis or a check-up. From this standpoint, an X-ray image photographing system has been proposed in which a reduced image data is generated from the X-ray image data, the reduced image data is transmitted to the console prior to transmitting the X-ray image data or the dark image data, and the preview image is displayed in the console (see, for example, Patent Document 1 (JP-A-2006-026083)).

SUMMARY OF THE INVENTION

In the X-ray image photographing system disclosed in Patent Document 1, the transmission of the reduced image data from the electronic cassette to the console begins right after acquiring the X-ray image data, but may reach to a dark image data acquisition period depending on the relationship between a data size and a communication speed.

When the transmission of the reduced image data reaches to a charge signal read-out period from the respective pixels in acquiring of the dark image data, for example, in an amplifier that amplifies charge signals read out from the respective pixels, electromagnetic noise accompanied by the communication is superimposed on the charge signal. Dark current of the respective pixels is very weak, and the correction process performed using the dark image data generated based on the charge signal on which the electromagnetic noise is superimposed may reduce the image quality of the X-ray image of the subject.

In view of above, an illustrative aspect of the invention is to provide a radiation image detection apparatus and a radiation image photographing system capable of performing a rapid display of the preview image without reducing the image quality of the X-ray image of the subject.

(1) According to an aspect of the invention, a radiation image detection apparatus includes: an imaging unit including an image receiving unit having a pixel array configured to receive radiation and to accumulate an electrical charge, and an image data generation unit configured to generate an image data based on the electrical charge output from the image receiving unit; a communication unit configured to transmit the image data acquired by the imaging unit to an external equipment; a communication speed detection unit configured to monitor the communication speed of the communication unit; and a control unit configured to drive the imaging unit so that a radiation image data is acquired during an exposure to radiation, the image receiving unit is reset after acquiring the radiation image data, and a dark image data is acquired during a non-exposure to the radiation; in which the image data generation unit generates a reduced image data from the radiation image data, and the control unit changes at least one of a reset time of the image receiving unit and a reduction ratio of the reduced image data on the basis of the communication speed detected by the communication speed detection unit such that the transmission of the reduced image data by the communication unit is completed at least prior to reading-out the electrical charge signal from the image receiving unit when acquiring the dark image.

(2) According to another aspect of the invention, a radiation image photographing system includes: the radiation image detection apparatus according to according to (1); and the external equipment configured to receive the image data transmitted from the radiation image detection apparatus, in which the external equipment includes; an image processing unit configured to generate a preview image data based on the reduced image data; and a display configured to display an image based on the preview image data generated by the image processing unit.

With the configuration of (1) or (2), when the image data generation unit generates the image data based on the charge signal output from the image receiving unit, the electromagnetic wave noise accompanied by the transmission of the reduced image data to the external equipment is prevented from being superimposed on the charge signal. Therefore, the preview image can be rapidly displayed without reducing the image quality of a radiation image of a subject.

BRIEF DESCRIPTION OF THE DRAWINGS

FIG. 6 is a timing chart illustrating the operations of a radio communication unit and the imaging unit of an electronic cassette constituting the X-ray image photographing system in accordance with the first embodiment of the present invention;

FIG. 8 is a timing chart illustrating the operations of a radio communication unit and the imaging unit of an electronic cassette constituting the X-ray image photographing system in accordance with a third exemplary embodiment of the present invention.

DETAILED DESCRIPTION OF EMBODIMENTS OF THE INVENTION

Hereinafter, the exemplary embodiments of the present invention are described with reference to the accompanying drawings. Herein, descriptions are made regarding an example in which the present invention is applied to an X-ray image photographing system installed in an X-ray radiography room in a hospital.

Figure 1:
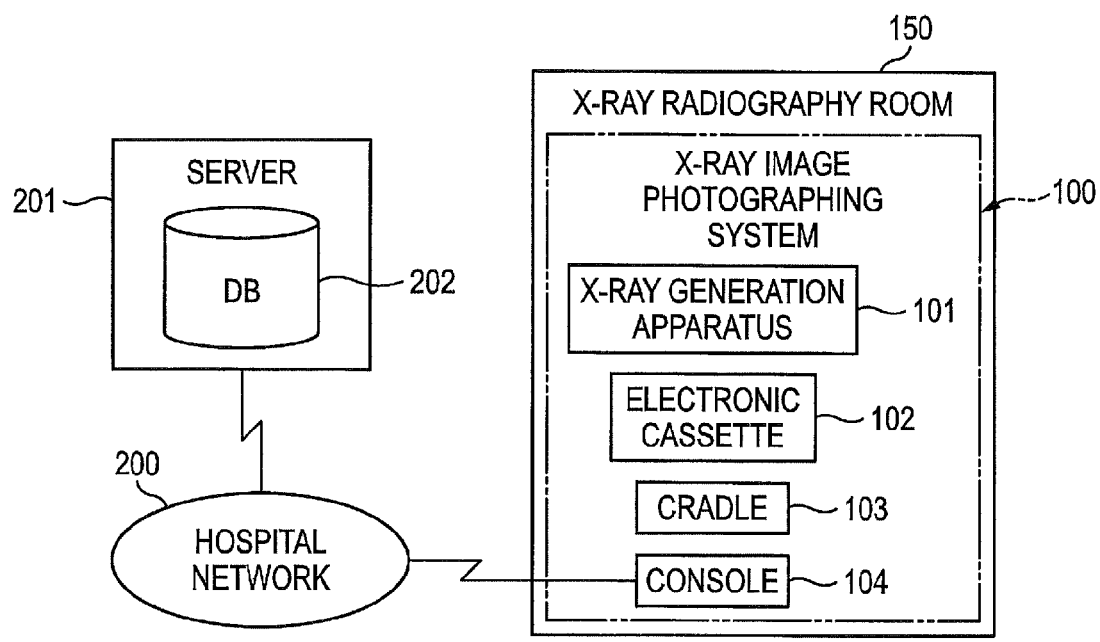
FIG. 1 is a block diagram illustrating a configuration of an X-ray image photographing system in accordance with a first exemplary embodiment of the present invention.

FIG. 1 is a view illustrating a configuration of an X-ray image photographing system in accordance with the embodiment of the present invention.

An X-ray image photographing system 100 includes an X-ray generation apparatus 101 that irradiates an X-ray to a subject (a patient), an electronic cassette (an X-ray image detection apparatus) 102 that receives the X-ray transmitted through the subject to generate an electrical charge and generate an X-ray image data based on the generated charge signal, a (battery charging) cradle 103 that charges a battery built-in the electronic cassette 102, and a console (an external equipment) 104 that receives the X-ray image data generated in the electronic cassette 102 to display an image or controls an X-ray generation apparatus 101 and the electronic cassette 102.

The X-ray image photographing system 100 is installed, for example, in a radiography room 150 within a hospital and connected to a server 201 through a hospital network 200, composed of, for example, a wireless local area network (LAN). The server 201 manages an X-ray image photographing schedule of the X-ray image photographing system 100, and includes a database 202 in which the information of the subject (patient), the information of the electronic cassette 102, and the information of an environment (an X-ray radiography room) in which the electronic cassette 102 is utilized are stored. The doctor or radiographer operates the X-ray image photographing system 100 in X-ray radiography room according to the instruction from the server 201 to perform the X-ray image photographing.

Figure 2:
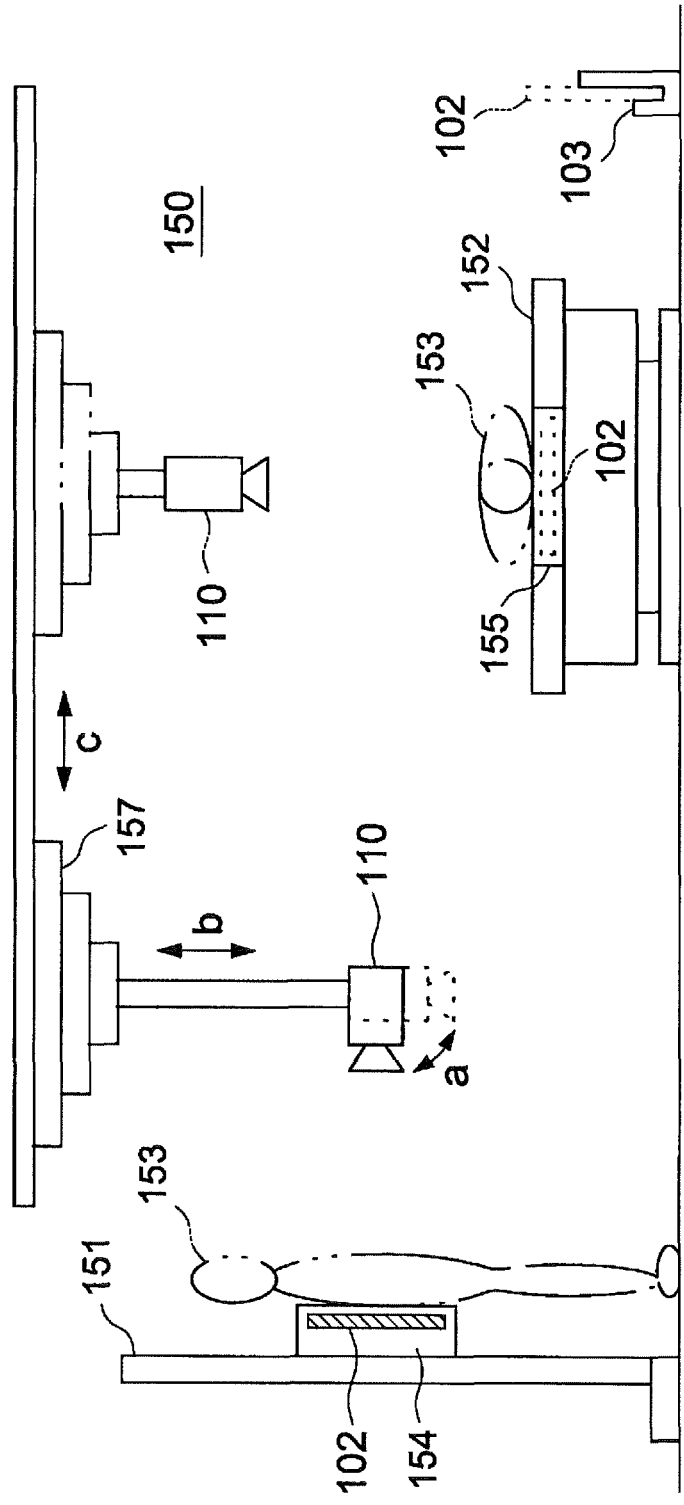
FIG. 2 is an explanatory view illustrating an example of arrangement of the respective apparatuses constituting the X-ray image photographing system in a radiation radiography room in accordance with a first exemplary embodiment of the present invention.

FIG. 2 is illustrates an arrangement example of the respective apparatuses constituting the X-ray image photographing system 100 in the X-ray radiography room.

As illustrated in FIG. 2, a vertical stand 151 used in performing an X-ray image photographing in standing position and a horizontal stand 152 used in performing an X-ray image photographing in supine position are installed in the X-ray radiography room 150. A front space of the vertical stand 151 corresponds to a photographing position of a subject 153 when performing the X-ray image photographing in a standing position and the upward space of the horizontal stand 152 corresponds to a photographing position of the subject 153 when performing the X-ray image photographing in a supine position.

A maintenance unit 154 maintaining the electronic cassette 102 is installed in the vertical stand 151 and the electronic cassette 102 is maintained in the maintenance unit 154 during the X-ray image photographing in a standing position. Similarly, a maintenance unit 155 maintaining the electronic cassette 102 is installed in the horizontal stand 152 and the electronic cassette 102 is maintained in the maintenance unit 155 during the X-ray image photographing in a supine position Further, the X-ray radiography room 150 is provided with a support movement mechanism 157 that supports a single X-ray source 110 to be rotatable about a horizontal axis (in a direction depicted by an arrow a shown in FIG. 2), to be movable in a vertical direction (a direction depicted in an arrow b shown in FIG. 2) and to be further movable in a horizontal direction (a direction depicted in an arrow c shown in FIG. 2), such that the X-ray image photographing in a standing position as well as in a supine position can be performed using the X-ray irradiated from the single X-ray source 110. Although not illustrated, the support movement mechanism 157 includes a driving source rotating the X-ray source 110 about a horizontal axis, a driving source moving the X-ray source 110 in a vertical direction, and a driving source moving the X-ray source 110 in horizontal direction.

The electronic cassette 102 when not in use is accommodated in the cradle 103 to charge a built-in battery (rechargeable battery). For performing the X-ray image photographing, the electronic cassette 102 is taken out from the cradle 103 and maintained either in the maintenance unit 154 of the vertical stand 151 or in the maintenance unit 155 of the horizontal stand 152.

Figure 3:
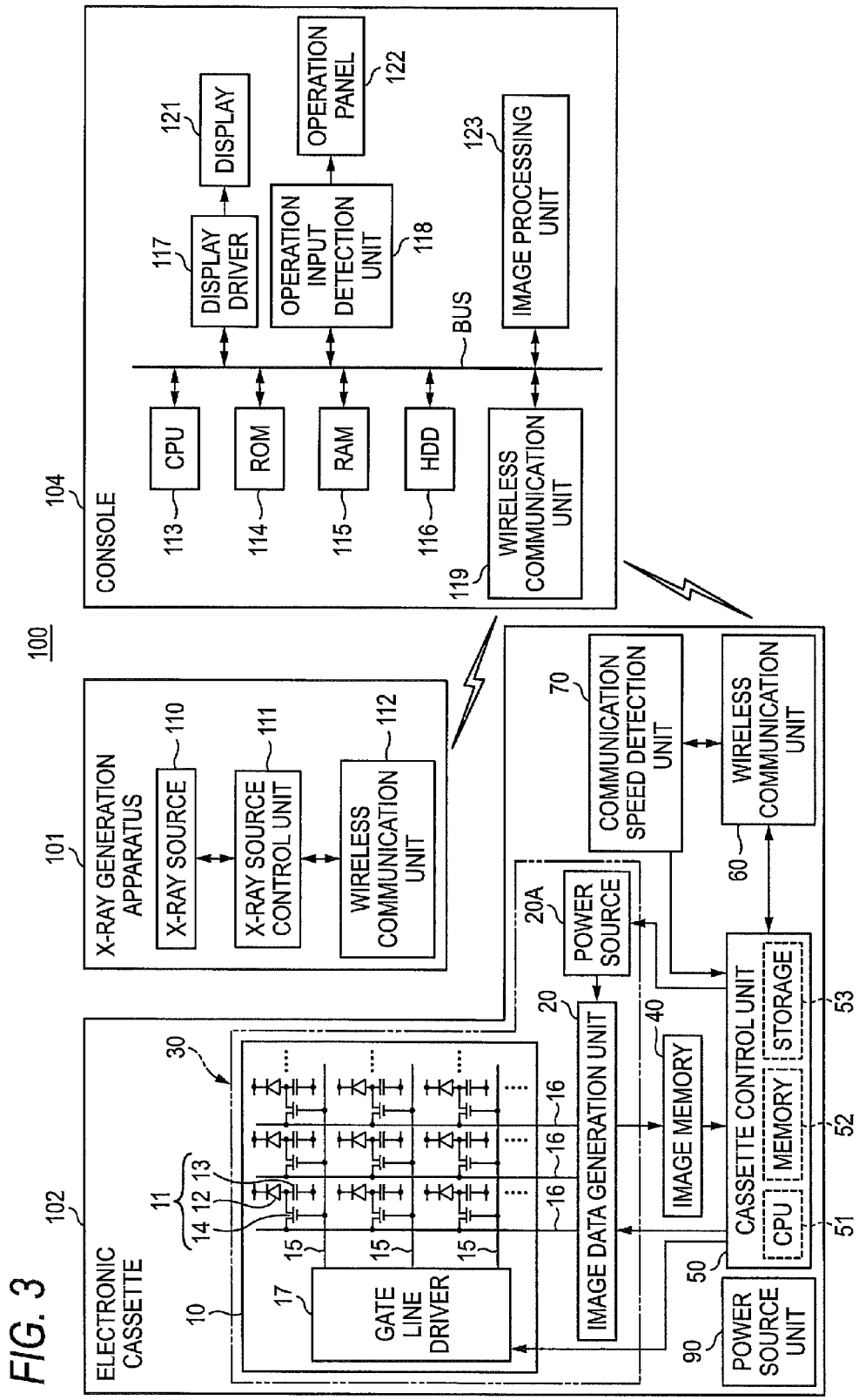
FIG. 3 is a block diagram illustrating a configuration of the major components of an electrical system constituting the X-ray image photographing system in accordance with the first embodiment of the present invention.

FIG. 3 is a block diagram illustrating a configuration of the major components of an electrical system constituting the X-ray image photographing system 100.

The X-ray image photographing system 100 has configuration in which various information are transmitted and received between the X-ray generation apparatus 101 and the electronic cassette 102, and between the electronic cassette 102 and the console 104.

As illustrated in FIG. 3, the electronic cassette 102 includes an imaging unit 30 having an image receiving unit 10 and an image data generation unit 20, an image memory 40, a cassette control unit 50, a wireless communication unit 60, a communication speed detection unit 70 and a power source unit 90.

The image receiving unit 10 is configured as an array in which a plurality of the pixels 11 receiving the X-ray transmitted through a body part to be photographed of the subject and accumulating the electrical charges are arranged in a row direction and in a column direction as illustrated in the FIG. 3, and each pixel 11 is configured to include a sensor unit 12, condenser 13 and a thin film transistor (TFT) 14.

The plurality of the pixels 11 are disposed in an intersection point between a plurality of gate wires 15 extending in a row direction and used in turning ON/OFF the thin film transistor 14 and a plurality of data wires 16 extending in a column direction and used in reading-out the charges through the TFT 14 being turned ON. Further, one end of each of the a plurality of gate wires 15 is connected to a gate line driver 17 and one end of each of the plurality of data wires 16 is connected to the image data generation unit 20.

The TFT 14 of the respective pixels 11 are sequentially turned ON in a unit of row through a signal supplied from the gate line driver 17 through the gate wires 15 and the charges read out from the TFT 14 being turned ON are sent to the data wires as the charge signals to be input to the image data generation unit 20. By doing this, the charges accumulated in the pixels 11 are read out in a unit of row to allow an X-ray image of the two dimensional form to be acquired.

Figure 4:
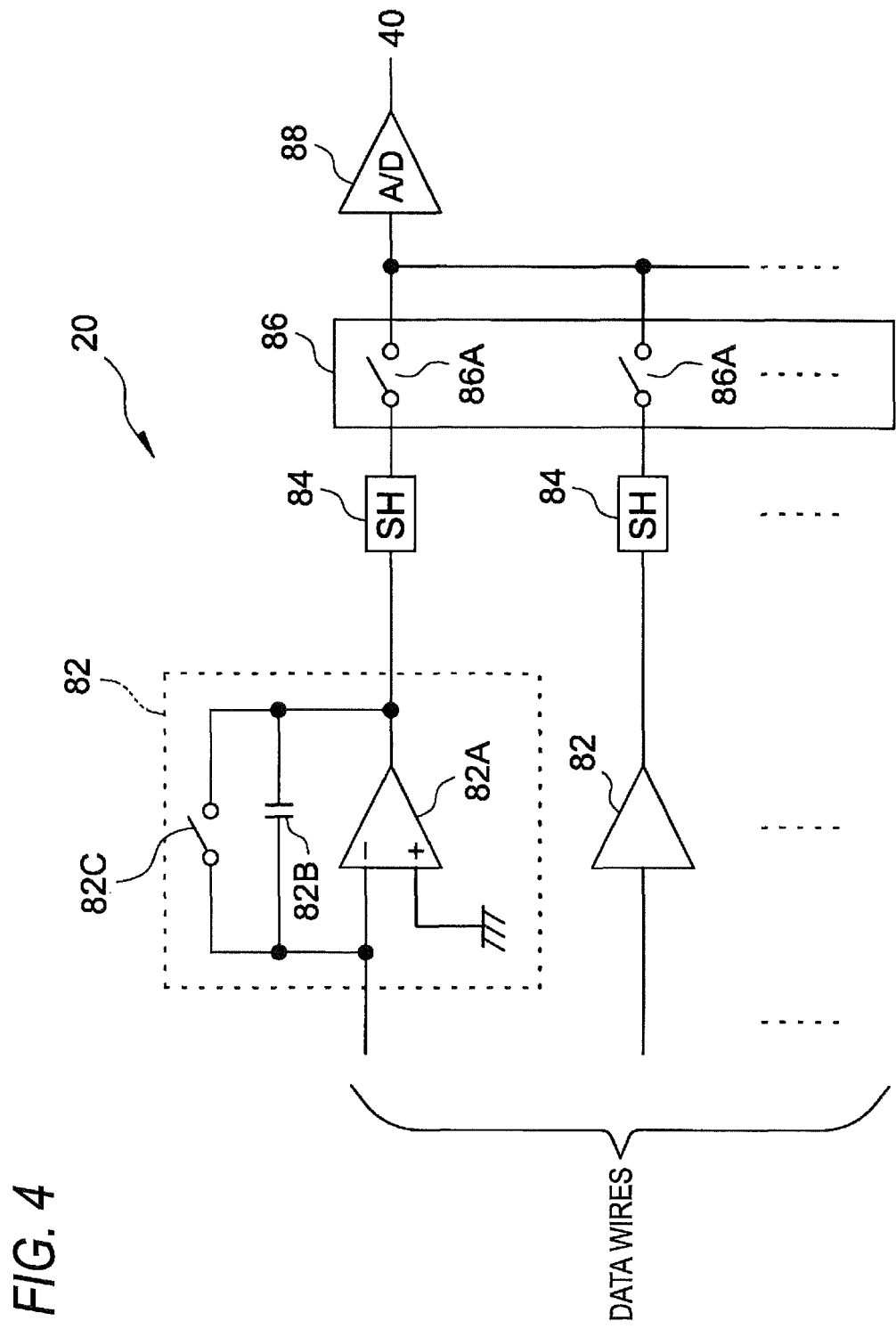
FIG. 4 is a circuit diagram illustrating an example of configuration of the image data generation unit illustrated in FIG. 3.

FIG. 4 is a circuit diagram illustrating an example of configuration of the image data generation unit 20.

As illustrated in FIG. 4, the image data generation unit 20 corresponds to the respective data wires 16 and includes a variable gain preamplifier 82 and a sample and hold circuit 84. Each of the sample and hold circuits 84 is connected to an analog-to-digital (A/D) converter 88 through a switch 86A installed in a multiplexer 86.

The respective variable gain preamplifier 82 includes an operation amplifier 82A of which positive input side is grounded, a condenser 82B connected in parallel between a negative input side and an output side of the operation amplifier 82A, and a reset switch 82C which is switched by a cassette control unit 50. The charge signal input to the image data generation unit 20 through the data wire 16 is accumulated in the condenser 82B of the variable gain preamplifier 82.

When detecting the X-ray image, the cassette control unit 50 first turns ON the reset switch 82C of the variable gain preamplifier 82 for a predetermined period of time to discharge the charges having been accumulated in the condenser 82B. Subsequently, the cassette control unit 50 drives the sample and hold circuit 84 for a predetermined period to maintain a signal level of the charge signal amplified by the variable gain preamplifier 82 in the sample and hold circuit 84.

The signal levels maintained in the sample and hold circuit 84 are sequentially selected according to the control of the cassette control unit 50 and converted from analog to digital by the A/D converter 88, such that an image data representing a photographed X-ray image is generated.

A power source 20A supplying a driving power to the imaging unit 30 and the image memory 40 storing the image data generated with the image data generation unit 20 are connected to the image data generation unit 20.

The power source 20A is constituted with a DC-DC converter of which power input terminal is connected to a power source unit 90. An output terminal of the DC-DC converter is connected to the variable gain preamplifier 82, the sample and hold circuit 84, the multiplexer 86, and the A/D converter 88 of the image data generation unit 20. Further, the cassette control unit 50 is connected to the control input terminal of the power source 20A to control the beginning and stopping of supplying power from the power source 20A.

The image memory 40 has a storage capacity capable of storing a predetermined number of image data, and stores the image data output from the A/D converter 88 of the image data generation unit 20 sequentially each time the X-ray image photographing is performed. Further, the cassette control unit 50 is connected to the image memory 40 to control the writing, reading out and erasing of the image data for the image memory 40.

The cassette control unit 50 is configured to include a microcomputer and provided with CPU 51, a memory 52 including ROM and RAM, and a non-volatile storage 53 including, for example, a flash memory to control an overall operation of the electronic cassette 102.

A wireless communication unit 60 is connected to the cassette control unit 50. The wireless communication unit 60 is conforming to wireless LAN standards of IEEE 802.11a/b/g/n, and transmits and receives various information between the X-ray generation apparatus 101 and a console 104 through a wireless communication based on the instruction from the cassette control unit 50.

The communication speed detection unit 70 is connected to the wireless communication, unit 60. The communication speed detection unit 70 monitors a communication speed of the wireless communication performed between the X-ray generation apparatus 101 and the console 104 based on the instruction issued from the cassette control unit 50.

Various circuits and devices (such as the gate line driver 17, the image data generation unit 20, the cassette control unit 50, the image memory 40, the wireless communication unit 60, and the communication speed detection unit 70) described above are operated with power supplied from the power source unit 90. The power source unit 90 incorporates a built-in battery built so as not to impair the portability of the electronic cassette 102 and supply power from the battery recharged with the cradle 103 (see FIG. 2) described above to the various circuits and devices. Additionally, wires connecting the power source unit 90 and the various circuits and devices are omitted in FIG. 3.

The X-ray generation apparatus 101 external to the electronic cassette 102 includes an X-ray source 110, the wireless communication unit 112 transmitting and receiving various information such as X-ray irradiation conditions to and from the console 104, and an X-ray source control unit 111 controls the X-ray source 110 based on X-ray irradiation conditions received from the console 104 and causes the X-ray source 110 to irradiate X-ray.

The console 104 includes the CPU 113, the ROM 114 having stored various programs including a control program in advance, the RAM 115 temporarily storing various information, a HDD 116 storing and maintaining various data, a display driver 117 controlling the displaying of various information onto a display (displaying unit) 121, an operation input detection unit 118 detecting a operation status to an operation panel 122, and the image processing unit 123 generating the preview data based on the reduced image data transmitted from the electronic cassette 102 or performing an offset correction based on the X-ray image data and a dark image data.

The console 104 includes the wireless communication unit 119 transmitting and receiving various information, such as the irradiation conditions, to and from the X-ray generation apparatus 101 via the wireless communication, and transmitting and receiving various information, such as the image data, to and from the electronic cassette 102.

The CPU 113, the ROM 114, the RAM 115, a FWD 116, a display driver 117 and the wireless communication unit 119 are connected with each other through a system bus. Accordingly, the CPU 113 can access the ROM 114, the RAM 115 and the HDD 116 and, control the displaying of various information on the display 121 through the display driver 117 and control the transmitting and receiving of the various information to and from the X-ray generation apparatus 101 and the electronic cassette 102 through the wireless communication unit 119. Further, the CPU 113 grasps the operation status of a user with respect to the operation panel 122 through the operation input detection unit 118.

Next, a photographing sequence of the X-ray image photographing system 100 will be described.

Figure 5:
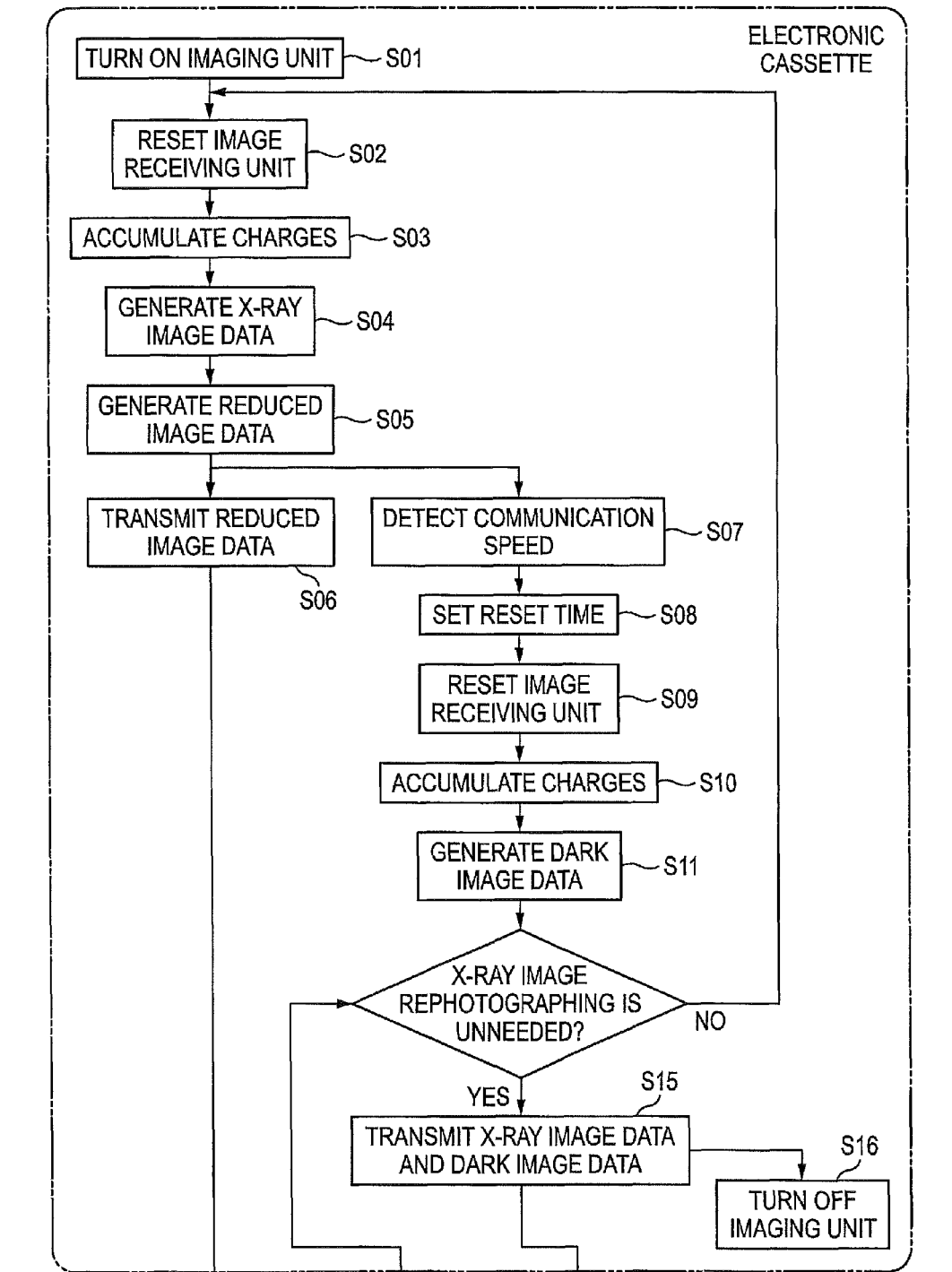
FIG. 5 is a flow chart illustrating a photographing sequence of the X-ray image photographing system in accordance with the first embodiment of the present invention.

FIG. 5 is a flow chart of the photographing sequence of the X-ray image photographing system 100 and FIG. 6 is a timing chart illustrating operations of the wireless communication unit and the imaging unit of the electronic cassette 102.

First, prior to beginning the X-ray image photographing, the power source unit 90 of the electronic cassette 102 is turned ON. In this case, the cassette control unit 50 controls the power source 20A to supply a driving power to the imaging unit 30 from the power source 20A (step 01).

Next, when the preparation of the X-ray image photographing is completed in the X-ray radiography room 150 as illustrated in FIG. 2, the pixels formed in the image receiving unit 10 of the electronic cassette 102 is reset (initialized) (step 02). In this case, the cassette control unit 50 drives the gate line drivers 17 of the image receiving unit 10 to output the ON signals sequentially to the gate wires 15 by one line and discharge the charges remaining in the condenser 13 of the pixels 11 formed on the image receiving unit 10 to the data wires 16.

Next, when the X-ray image photographing is started and X-ray transmitted through the body part to be photographed of a subject enters into the image receiving unit 10, the electrical charges corresponding to the intensity of X-ray are generated in the respective pixels 11 formed in the image receiving unit 10 and accumulated in condensers 13 of the respective pixels 11 (step 03).

Next, when the X-ray image photographing is completed and the irradiation of X-ray into the image receiving unit 10 is stopped, the reading-out of the charges accumulated in the pixels 11 of the image receiving unit 10 begins. In this case, the cassette control unit 50 drives the gate line drivers 17 of the image receiving unit 10 to output the ON signals sequentially to the respective gate wires 15 by one line and sequentially turns ON the thin film transistor 14 of the pixels 11 connected to the respective gate wires 15 by one line.

By doing this, the charges accumulated in the condenser 13 are sent to the data wires 16 as a charge signal from the pixel 11 in which the thin film transistor 14 is turned ON and input to the image data generation unit 20 connected to the data wires 16. The image data generation unit 20 amplifies the charge signal with the variable gain preamplifier 82 and then performs A/D conversion for the amplified charge signal to generate a digital image data corresponding to the photographed X-ray image data (step 04) and stores the X-ray image data into the image memory 40.

Next, the cassette control unit 50 drives the image data generation unit 20 to generate the reduced image data for low resolution preview based on the X-ray image data stored in the image memory 40 (step 05). The reduced image data can be generated from the X-ray image data using, such as for example, a well-known binning method or thinning method in which one pixel group is extracted among the pixel groups constituting the square areas of a number of n×n pixels 11 formed on the image receiving unit 10 and is subjected to an operation such that one pixel of the reduced image data representing the square area of the number of n×n pixels 11 is generated.

When the image data generation unit 20 generates the reduced image data, the cassette control unit 50 drives the wireless communication unit 60 to transmit the reduced image data to the console 104 through wireless communication (step 06). In this case, the communication speed detection unit 70 connected to the wireless communication unit 60 monitors the communication speed of the reduced image data transmitted to the console 104 from the wireless communication unit 60. The cassette control unit 50 detects the communication speed monitored by the communication speed detection unit 70 (step 07) and stores the detected communication speed to the storage 53.

Next, the cassette control unit 50 sets a reset time (T) based on the detected communication speed (step 08), and subsequently, drives the image receiving unit 10 to reset the respective pixels 11 (step 09). That is, the cassette control unit 50 drives the gate line driver 17 to output ON signals sequentially to the respective gate wires 15 by one line, and discharges the very small charges remaining on the condenser 13 of the respective pixels 11 to the data wires 16.

Next, the cassette control unit 50 drives the image receiving unit 10 and repeats the same operation as the X-ray image photographing for the same period while not being subjected to the X-ray irradiation, such that the charges are accumulated in the respective pixels 11 of the image receiving unit 10 (step 10), and subsequently, the charges accumulated in the respective pixels are read out in the same sequence as the reading out of the charges at step 04. When the charge signals read out from the respective pixels 11 are input to the image data generation unit 20 through the data wires 16, the image data generation unit 20 generates the dark image data from the charge signals (step 11) and stores the dark image data in the image memory 40.

In the meantime, the reduced image data for preview generated in the image data generation unit 20 is transmitted to the console 104 by the wireless communication unit 60 through the wireless communication (step 06) while electric charge is being accumulated in the image receiving unit 10 (step 10).

If the transmission period of the reduced image data at step 06 reaches the reading out period of the charges at step 10, when image data generation unit 20 generates the dark image data, the electromagnetic wave accompanied by the wireless communication of the reduced image data influence on, for example, the variable gain preamplifier 82 of the image data generation unit 20. As a result, signal noise may be superimposed on the charges being read out to reduce the accuracy of the offset correction performed using the dark image data.

Therefore, in the X-ray image photographing system 100, the cassette control unit 50 changes the reset time (T) set at step 09, such that the transmission of the reduced image data from the wireless communication unit 60 to the console 104 is completed prior to beginning of reading out the charges subsequently to step 10, that is, within a period during which electrical charges are accumulated in the respective pixels 11 of the image receiving unit 10 while not being subjected to the X-ray irradiation.

Specifically, when a minimum time required to reset at step 09 is $t_0$, and a transmission time of the reduced image data (reduced image data capacity/communication speed) calculated from a communication speed detected at step 07 and a reduced image data capacity generated at step 05 is t, if $t > t_0$, the reset time (T) is set to T=t (or, a value larger than t), and otherwise, if t≤$t_0$, the reset time (T) is set to T=$t_0$.

By doing this, when the reduced image data is transmitted from the electronic cassette 102 to the console 104 at step 06, the image processing unit 123 of the console 104 performs a offset correction using the transmitted dark image data and the dark image data acquired in the previous photographing time and stored in the HDD 116 in advance (step 12), and generates a preview image data based on the reduced image data acquired by the offset correction.

Next, the preview image data generated by the image processing unit 123 is transmitted to the display 121 through the system bus (BUS) and the display driver 117 to be displayed as an image for preview (step 13).

Additionally, at step 13, the image data for preview may be directly generated from the reduced image data transmitted to the console 104. However, when the image data for preview is generated based on the reduced image data acquired by the offset correction, the quality of the preview image displayed on the display 121 can be improved as compared to a case where the image data for preview is directly generated from the reduced image data.

When the preview image is displayed on the display 121, a doctor or a radiographer observes the preview image, checks whether the body part to be photographed of the subject e is properly displayed or not, and determine whether the X-ray rephotographing is needed or not (step 14). The determined result is input to the console 104 and the information of the input determination result is transmitted from the console 104 to the electronic cassette 102.

When it is determined that the X-ray image rephotographing is not needed, the image data and the dark image data stored in the image memory 40 is transmitted to the console 104 by the control of the cassette control unit 50 through the wireless communication unit 60 (step 15), and the power source 20A of the imaging unit 30 is turned OFF (step 16). In this case, when the reduced image transmitted at step 06 corresponds to a thinned data, the image data to be transmitted at step 15 may be a remaining image data, other than the thinned data, of the thinned image transmitted at step 06. When an image to be transmitted is not a full image but the remaining image data of the thinned image, there is a merit that a transmission time becomes shorter.

When the X-ray image data and the dark image data are transmitted to the console 104, the image processing unit 123 stores the dark image data to the HDD 116 first (step 17), and subsequently, performs the offset correction for the X-ray image data using the dark image data (step 18). Thereafter, a gain correction and a defect correction for the X-ray image data offset corrected, such that the X-ray image for diagnosis and check-up of the subject is displayed on the display 121 (step 19).

In the meantime, when it is determined that the X-ray image rephotographing is needed at step 14, power is continuously supplied to the imaging unit 30 by the control of the cassette control unit 50 and the processing steps after step 02 are repeated.

Additionally, although in the above-description, the doctor or radiographer determines whether the X-ray image rephotographing is needed or not, it may be possible to make the image processing unit 123 of the console 104 to automatically determine whether the X-ray image rephotographing is needed or not, such as for example, analyzing contrast of the preview image data to determine whether the X-ray dose for the X-ray image photographing is appropriate or not, through the image processing for the preview image data. When it is determined that the X-ray image rephoto graphing is not needed, the console 104 instructs the cassette control unit 50 to perform the steps 15 and 16 described above. Meanwhile, when it is determined that the X-ray image rephotographing is needed, the console 104 instructs the cassette control unit 50 to continuously supply power to the imaging unit 30 and repeat the processing steps after step 02.

As described above, in the X-ray image photographing system 100, when the reduced image data for preview generated in the image data generation unit 20 is transmitted to the console 104 through the wireless communication, the cassette control unit 50 changes the reset time (T) of the image receiving unit 10 based on the communication speed detected by the communication speed detection unit 70, such that the transmission of the reduced image data to the console 104 is completed prior to beginning of the reading out of the charge signal for acquiring the dark image data.

By doing this, when the image data generation unit 20 generates the dark image data, it is possible to prevent noise from being superimposed on the charge signal read out due to the electronic wave accompanied by the wireless communication of the reduced image data. Therefore, the preview image can be rapidly displayed without reducing the quality of the X-ray image of the subject.

Figure 7:
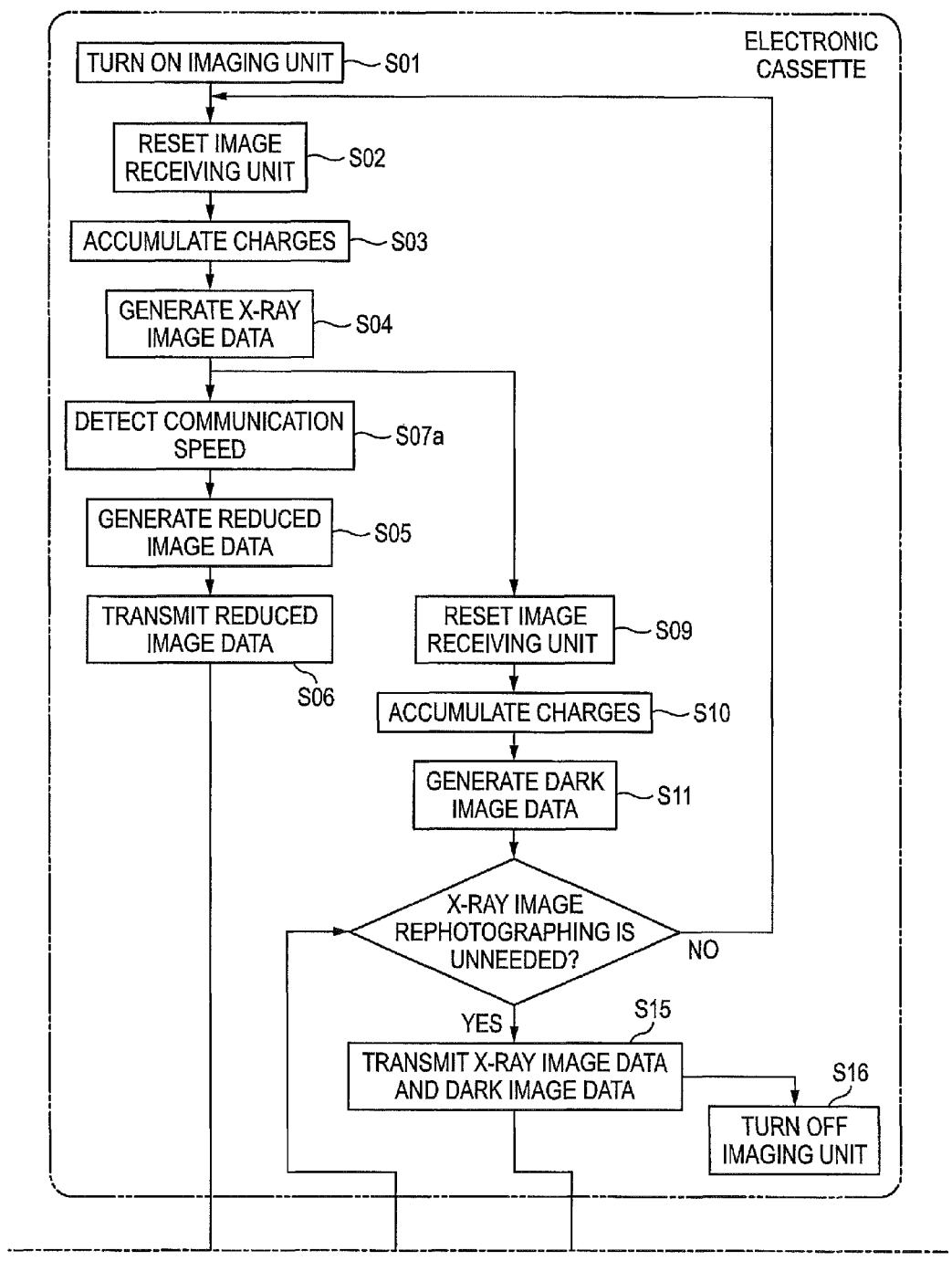
FIG. 7 is a flow chart illustrating a photographing sequence of an X-ray image photographing system in accordance with a second exemplary embodiment of the present invention.

FIG. 7 is another example of the flow chart illustrating the photographing sequence of the X-ray image photographing system 100.

In the example illustrated in FIG. 5, when the reduced image data for preview in the image data generation unit 20 is transmitted to the console 104 through wireless communication, the cassette control unit 50 changed the reset time (T) of the image receiving unit 10 based on the communication speed detected by the communication speed detection unit 70, such that the transmission of the reduced image date to the console 104 is completed prior to beginning of the reading out of the charge signals for acquiring the dark image.

In contrast, in this example, as illustrated in FIG. 7, the reduction ratio of the reduced image date based on the communication speed detected by the communication speed detection unit 70 is changed, so that the transmission of the reduced image date to the console 104 is completed prior to beginning of the reading out of the charge signals for acquiring the dark image. When the thinning method described above is used in generating the reduced image data, the thinning ratio, that is, a size of the square area of n×n pixels in the X-ray image data corresponding to one pixel in the reduced image data, is adjusted to make it possible to appropriately change the reduction ratio of the reduced image data.

First, the X-ray image data is generated according to step 01 to step 04 described above and the generated X-ray image data is stored in the image memory 40.

Next, the cassette control unit 50 drives the image receiving unit 10 to reset (initialize) the respective pixels 11 (step 09) and detects the communication speed monitored by the communication speed detection unit 70 (step 07a).

Next, the cassette control unit 50 calculates a transmittable image data capacity $S_0$ (communication speed×reset time $t_0$) from the detected communication speed at step 07a and the reset time $t_0$ set initially.

Further, the cassette control unit 50 set the reduction ratio of the reduced image data to generate the reduced image data, such that the reduced image data capacity is equal to or less than the transmittable image data capacity $S_0$ (step 05), and subsequently, the reduced image data is transmitted to the console 104 through the wireless communication unit 60 (step 06).

The remaining flow (step 10 to step 19) is the same as those illustrated in FIG. 5, and the description thereof will be omitted.

As described above, when the image data generation unit 20 generates the dark image data, it is possible to prevent noise from being superimposed on the charge signal read out due to the electronic wave accompanied by the wireless communication of the reduced image data. Therefore, the preview image can be rapidly displayed without reducing the quality of the X-ray image of the subject.

FIG. 8 is another timing chart illustrating the operations of the wireless communication unit and the imaging unit of the electronic cassette 102.

In the examples as described above, the cassette control unit 50 changed the reset time or the reduction ratio of the reduction image data such that the transmission of the reduced image date from wireless communication unit 60 to the console 104 is completed prior to beginning of reading out of the charge signals for acquiring the dark image.

In contrast, in the present example, as illustrated in FIG. 8, the cassette control unit 50 changes the reset time set at step 08 such that the transmission of the reduced image date from the wireless communication unit 60 to the console 104 (step 06) is completed prior to beginning of accumulating of the charges (step 10) for acquiring the dark image. Otherwise, the reduction ratio of the reduction image data may be changed instead of changing the reset time. Accordingly, it is possible to prevent the charges accumulated in the respective pixels 11 from being influenced by the electronic wave accompanied by wireless communication of the reduced image data.

In the description as described above, although either the reset time or the reduction ratio of the reduction image data is changed such that the transmission of the reduced image date from the wireless communication unit 60 to the console 104 is completed prior to beginning of the reading out of the charge signals for acquiring the dark image, both the reset time and the reduction ratio of the reduction image data may be changed.

In the description as described above, although the X-ray image photographing system and the X-ray image detection apparatus that transmit the image data to the external equipment through wireless communication, the present invention may be applied to an X-ray image photographing system and an X-ray image detection apparatus that transmit the image data to the external equipment through wire communication.

In the description as described above, a general X-ray is used as the radiation, but the present invention is not limited the X-ray and radiation other than X-ray such as α ray or γ ray may be utilized.

As described above, the radiation image detection apparatus as described in the following (1) to (4), the radiation image photographing system as described in the following (5) to (7), and the control method of the radiation image detection apparatus described in the following (8) and (9) are disclosed.

(1) A radiation image detection apparatus includes: an imaging unit including an image receiving unit having a pixel array configured to receive radiation and to accumulate an electrical charge, and an image data generation unit configured to generate an image data based on the electrical charge output from the image receiving unit; a communication unit configured to transmit the image data acquired by the imaging unit to an external equipment; a communication speed detection unit configured to monitor the communication speed of the communication unit; and a control unit configured to drive the imaging unit so that a radiation image data is acquired during an exposure to radiation, the image receiving unit is reset after acquiring the radiation image data, and a dark image data is acquired during a non-exposure to the radiation; in which the image data generation unit generates a reduced image data from the radiation image data, and the control unit changes at least one of a reset time of the image receiving unit and a reduction ratio of the reduced image data on the basis of the communication speed detected by the communication speed detection unit such that the transmission of the reduced image data by the communication unit is completed at least prior to reading-out the electrical charge signal from the image receiving unit when acquiring the dark image.

(2) In the radiation image detection apparatus according to (1), the control unit changes at least one of the reset time of the image receiving unit and the reduction ratio of the reduced image data on the basis of the communication speed detected by the communication speed detection unit such that the transmission of the reduced image data by the communication unit is completed at least prior to accumulating the electrical charge signal from the image receiving unit when acquiring the dark image.

(3) In the radiation image detection apparatus according to (1) or (2), the control unit is configured to stop or continue supplying of power to the imaging unit on the basis of a control signal from the external equipment after acquisition of the dark image data.

(4) In the radiation image detection apparatus according to any one of (1) to (3), the communication unit is configured to transmit the image data to the external equipment through a wireless communication.

(5) A radiation image photographing system includes: the radiation image detection apparatus according to according to any one of (1) to (4); and the external equipment configured to receive the image data transmitted from the radiation image detection apparatus, in which the external equipment includes; an image processing unit configured to generate a preview image data based on the reduced image data; and a display configured to display an image based on the preview image data generated by the image processing unit.

(6) In the radiation image photographing system according to (5), the external equipment includes a storage storing the dark image data, and the image processing unit generates the preview image data by performing a correction processing to the reduced image data using a previous dark image data stored in the storage.

(7) In the radiation image photographing system according to (5) or (6), the external equipment includes a determination unit configured to determine, on the basis of the preview image data, whether a photographing conducted at the time of acquiring the reduced image data being source of the preview image data is appropriate or not, and when it is determined that the photographing is appropriate, the control unit stops supplying power to the imaging unit after acquisition of the dark image data, and when it is determined that the photographing is not appropriate, the control unit continues supplying power to the imaging unit after acquisition of the dark image data.

(8) A method of controlling a radiation image detection apparatus, the radiation image detection apparatus including: an imaging unit that includes an image receiving unit having a pixel array configured to receive radiation and to accumulate an electrical charge, and an image data generation unit configured to generate an image data based on the electrical charge output from the image receiving unit; a communication unit configured to transmit the image data acquired by the imaging unit to an external equipment; a communication speed detection unit configured to monitor the communication speed of the communication unit; and a control unit configured to drive the imaging unit so that a radiation image data is acquired during an exposure to radiation, the image receiving unit is reset after acquiring the radiation image data, and a dark image data is acquired during a non-exposure to the radiation, in which the method comprises: changing at least one of a reset time of the image receiving unit and a reduction ratio of the reduced image data on the basis of the communication speed detected by the communication speed detection unit such that the transmission of the reduced image data by the communication unit is completed at least prior to reading-out of the electrical charge signal from the image receiving unit when acquiring the dark image.

(9) In the method of controlling a radiation image detection apparatus according to (8), at least one of a reset time of the image receiving unit and a reduction ratio of the reduced image data is changed by the control unit on the basis of the communication speed detected by the communication speed detection unit such that the transmission of the reduced image data by the communication unit is completed at least prior to accumulating the electrical charge signal from the image receiving unit when acquiring the dark image.

What is claimed is:

1. A radiation image detection apparatus, comprising:
an imaging unit including an image receiving unit having a pixel array configured to receive radiation and to accumulate an electrical charge, and an image data generation unit configured to generate an image data based on the electrical charge output from the image receiving unit;
a communication unit configured to transmit the image data acquired by the imaging unit to an external equipment;
a communication speed detection unit configured to monitor the communication speed of the communication unit; and
a control unit configured to drive the imaging unit so that a radiation image data is acquired during an exposure to radiation, the image receiving unit is reset after acquiring the radiation image data, and a dark image data is acquired during a non-exposure to the radiation;
wherein the image data generation unit generates a reduced image data from the radiation image data, and
the control unit changes at least one of a reset time of the image receiving unit and a reduction ratio of the reduced image data on the basis of the communication speed detected by the communication speed detection unit such that the transmission of the reduced image data by the communication unit is completed at least prior to reading-out the electrical charge signal from the image receiving unit when acquiring the dark image.

2. The radiation image detection apparatus according to claim 1, wherein:
the control unit changes at least one of the reset time of the image receiving unit and the reduction ratio of the reduced image data on the basis of the communication speed detected by the communication speed detection unit such that the transmission of the reduced image data by the communication unit is completed at least prior to accumulating the electrical charge signal from the image receiving unit when acquiring the dark image.

3. The radiation image detection apparatus according to claim 1, wherein:
the control unit is configured to stop or continue supplying of power to the imaging unit on the basis of a control signal from the external equipment after acquisition of the dark image data.

4. The radiation image detection apparatus according to claim 1, wherein:
the communication unit is configured to transmit the image data to the external equipment through a wireless communication.

5. A radiation image photographing system comprising:
the radiation image detection apparatus according to according to claim 1; and
the external equipment configured to receive the image data transmitted from the radiation image detection apparatus,
wherein the external equipment includes:
an image processing unit configured to generate a preview image data based on the reduced image data; and
a display configured to display an image based on the preview image data generated by the image processing unit.

6. The radiation image photographing system according to claim 5, wherein:
the external equipment includes a storage storing the dark image data, and
the image processing unit generates the preview image data by performing a correction processing to the reduced image data using a previous dark image data stored in the storage.

7. The radiation image photographing system according to claim 5, wherein:
the external equipment includes a determination unit configured to determine, on the basis of the preview image data, whether a photographing conducted at the time of acquiring the reduced image data being source of the preview image data is appropriate or not, and
when it is determined that the photographing is appropriate, the control unit stops supplying power to the imaging unit after acquisition of the dark image data, and
when it is determined that the photographing is not appropriate, the control unit continues supplying power to the imaging unit after acquisition of the dark image data.

8. A method of controlling a radiation image detection apparatus, the radiation image detection apparatus including:
an imaging unit that includes an image receiving unit having a pixel array configured to receive radiation and to accumulate an electrical charge, and an image data generation unit configured to generate an image data based on the electrical charge output from the image receiving unit; a communication unit configured to transmit the image data acquired by the imaging unit to an external equipment; a communication speed detection unit configured to monitor the communication speed of the communication unit; and a control unit configured to drive the imaging unit so that a radiation image data is acquired during an exposure to radiation, the image receiving unit is reset after acquiring the radiation image data, and a dark image data is acquired during a non-exposure to the radiation,
wherein the method comprises:
changing at least one of a reset time of the image receiving unit and a reduction ratio of the reduced image data on the basis of the communication speed detected by the communication speed detection unit such that the transmission of the reduced image data by the communication unit is completed at least prior to reading-out of the electrical charge signal from the image receiving unit when acquiring the dark image.

9. The method of controlling a radiation image detection apparatus according to claim 8, wherein:
at least one of a reset time of the image receiving unit and a reduction ratio of the reduced image data is changed by the control unit on the basis of the communication speed detected by the communication speed detection unit such that the transmission of the reduced image data by the communication unit is completed at least prior to accumulating the electrical charge signal from the image receiving unit when acquiring the dark image.

* * * * *